United States Patent [19]

Petzoldt et al.

[11] 4,435,327

[45] Mar. 6, 1984

[54] 3β,7β,15α-TRIHYDROXY-5-ANDROSTEN-17-ONE, ITS 3,15-DIPIVALATE, AND THEIR PREPARATION

[75] Inventors: Karl Petzoldt; Henry Laurent; Rudolf Wiechert, all of Berlin, Fed. Rep. of Germany

[73] Assignee: Schering, Aktiengesellschaft, Berlin and Bergkamen, Fed. Rep. of Germany

[21] Appl. No.: 420,674

[22] Filed: Sep. 21, 1982

[30] Foreign Application Priority Data

Sep. 21, 1981 [DE] Fed. Rep. of Germany ....... 3137919

[51] Int. Cl.³ .............................................. C07J 1/00
[52] U.S. Cl. ............................. 260/397.5; 260/239.57
[58] Field of Search ..................................... 260/397.5

[56] References Cited

PUBLICATIONS

P. Morand and A van Tongerloo, Steroids 21: 47 (1973).
L. Ruzicka, V. Prelong, and E. Tagmann, Helv. Chim. Acta 27: 1149 (1944).
Chemical Abstracts, vol. 91 (1979) Par. 123928(v).

Primary Examiner—Elbert L. Roberts
Attorney, Agent, or Firm—Millen & White

[57] ABSTRACT

A process for the preparation of 3β,7β,15α-trihydroxy-5-androsten-17-one and the 3,15-dipivalate thereof comprises epimerizing 3β,7α,15α-trihydroxy-5-androsten-17-one in the presence of a ketone with or without a solvent, with dilute mineral acid and subsequent treatment with an organic base, and optionally subsequently esterifying the 3β- and 15α-positions of the resultant 3β,7β,15α-triol with a reactive derivative of pivalic acid.

14 Claims, No Drawings

3β,7β,15α-TRIHYDROXY-5-ANDROSTEN-17-ONE, ITS 3,15-DIPIVALATE, AND THEIR PREPARATION

BACKGROUND OF THE INVENTION

The present invention relates to a method for preparing the title compounds and the compounds per se.

As is known, 3β-hydroxy-Δ$^5$-steroids can be converted to 3β,7β-dihydroxy-Δ$^5$-steroids by allyl oxidation of the corresponding 3-acetates with chromium(VI) oxide in the presence of 3,5-dimethylpyrazole or with tert-butyl chromate and subsequent reduction of the 7-keto group with lithium tri-tert-butoxyalanate.

However, these processes have the disadvantages that the yields are relatively low and that they are inapplicable to steroids containing additional reactive groups, such as 17-keto and 15-hydroxy groups.

SUMMARY OF THE INVENTION

Accordingly, it is an object of the present invention to provide a process which overcomes these disadvantages.

Upon further study of the specification and appended claims, further objects and advantages of this invention will become apparent to those skilled in the art.

These objects of this invention have been attained by combining 3β,7α,15α-trihydroxy-5-androsten-17-one (obtainable from 3β-hydroxy-5-androsten-17-one in high yield by conventional microbiological hydroxylation with *Colletotrichum lini*), in the presence of a ketone and, optionally, a solvent with a dilute mineral acid and, subsequently, with an organic base; and, optionally, then esterifying the thus-obtained 3β,7β,15β-triol in a manner known per se in the 3β- and 15α-positions with a reactive derivative of pivalic acid.

This invention also relates to the products of the reaction.

DETAILED DISCUSSION

Suitable reaction compatible solvents include halogenated hydrocarbons, such as dichloromethane, 1,2-dichloroethane, and trichloromethane. The amount of solvent is not critical and usually is 1-10 wt. % based on the amount of starting material steroid.

Actually, all cyclic and straight-chain aliphatic ketones of up to 6 carbon atoms are suitable for conducting the reaction of this invention. Examples include 2-propanone, 2-butanone, 2-pentanone, 3-pentanone, methyl isobutyl ketone, cyclopentanone, and cyclohexanone. The use of 2-propanone and methyl isobutyl ketone is preferred. The amount of ketone added is variable within wide limits. However, a quantity of 10-100 molar equivalents, based on the amount of starting material employed, is expedient.

A dilute mineral acid is understood to include within the scope of this invention, an acid of 10-50 vol-% strength in an amount of 0,1-1 moles based on the number of moles of starting material. Suitable acids include, for example, sulfuric acid, perchloric acid, and hydrochloric acid, perchloric acid preferably being utilized. However, also suitable are strong organic acids, such as p-toluenesulfonic acid and trifluoroacetic acid and others known as equivalents of the mineral acids, in the same strengths.

This stage of the reaction is usually conducted at 0°-50° C., preferably at 10°-20° C. for 1-24 hours, preferably 2-5 hours. This stage is usually conducted under an inert atmosphere such as nitrogen and under agitation.

After completion of the first stage, an organic base is added to the epimerized product either in situ or after separation of the latter from its reaction medium. Suitable bases include pyridine, diethylamine, triethylamine, preferably, pyridine is used. The amount of base is usually 2-10 wt. %, based on the amount of 7α-starting material used.

This stage of the reaction* takes place at 5°-50° C., preferably 15°-20° C., over a time period of 2-48 hours, preferably 20-24 hours, usually under agitation.

*treatment with base and esterification

The reaction of this invention represents a direct, quantitative epimerization of an allyl-positioned 7α-hydroxy group. The course of this reaction could not have been foreseen.

This is so, because heretofore it has never been possible to obtain the pure 7β-epimers, starting with 7α-hydroxy- or 7α-acetoxy-Δ$^5$-steroids, under solvolysis conditions. Thus, the treatment of 3β-acetoxy-5-cholesten-7α-ol with 80% acetic acid at room temperature, for example, after 6 hours results in a 50-60% yield of an epimeric mixture made up of 7α-acetoxy- and 7β-acetoxy-Δ$^5$-compounds [P. Morand and A. van Tongerloo, Steroids 21: 47 (1973); cf. also L. Ruzicka, V. Prelog, and E. Tagmann, Helv. Chim. Acta 27: 1149 (1944)].

The subsequent, optional partial esterification of the 3β- and 15α-hydroxy groups with pivalic acid or reactive derivatives thereof, e.g., the acid chloride or anhydride, takes place according to conventional methods. This reaction can be performed either after isolation of the 3β,7β,15α-triol from the reaction medium or immediately, i.e., in situ without isolation of the triol.

For this purpose, in the former case, the triol is usually dissolved in pyridine and esterified with pivalic acid chloride in the presence of a conventional esterification catalyst, such as 4-dimethylaminopyridine. In the latter instance, the pyridine solution of the triol is subjected to such esterification conditions without any intermediate working-up procedure, as indicated above.

The esterified or non-esterified reaction product is worked up fully conventionally as usual after the reaction is completed, such as, for example by precipitation, extraction, recrystallization and/or chromatography.

The 3β,7β,15α-triol and/or its 3,15-diester, producible according to this invention, is an intermediate for the preparation of highly efficacious antialdosterones, such as, for example, 6β,7β;15β,16β-dimethylene-3-oxo-17α-pregn-4-ene-21,17-carbolactone. See, e.g., DOS No. 2,652,761 whose disclosure is incorporated by reference herein.

Use of the 3β,7β,15α-triol of this invention for the preparation of such an aldosterone antagonist is especially advantageous for the reason that the previously required 15-stage synthesis, starting with 3β-hydroxy-5-androsten-17-one, is shortened by three stages. In this connection, a more than three fold increase in yield is achieved.

The 15-stage synthesis of 6β,7β;15β,16β-dimethylene-3-oxo-17α-pregn-4-ene-21,17-carbolactone proceeds by way of the following reaction stages:

1. ketalizing 3β-hydroxy-5-androsten-17-one with ethylene glycol to form 17,17-ethylenedioxy-5-androsten-3β-ol;

2. brominating in the 16-position to form 16α-bromo-17,17-ethylenedioxy-5-androsten-3β-ol;

3. splitting off hydrogen bromide with formation of 17,17-ethylenedioxy-5,15-androstadien-3β-ol;

4. splitting of the ketal, thus obtaining 3β-hydroxy-5,15-androstadien-17-one;

5. methylenating the $\Delta^{15}$-double bond according to Corey and Chaykovsky, J. Am. Soc. 84 (1962) 3782, to form 3β-hydroxy-15β-, 16β-methylene-5-androsten-17-one.

6. microbiologically hydroxylating the 7-position to form 3β,7β-dihydroxy-15β,16β-methylene-5-androsten-17-one;

7. esterifying the 3β-hydroxy group to form 7β-hydroxy-15β,16β-methylene-3β-pivaloyloxy-5-androsten-17-one;

8. epoxidizing the $\Delta^5$-double bond to form 5,6β-epoxy-7β-hydroxy-15β,16β-methylene-3β-pivaloyloxy-5β-androstan-17-one;

9. substituting the 7β-OH by 7α-chlorine with formation of 7α-chloro-5,6β-epoxy-15β,16β-methylene-3β-pivaloyloxy-5β-androstan-17-one;

10. splitting the resultant epoxide compound and eliminating chlorine therefrom to form 5-hydroxy-15β,16β-methylene-3β-pivaloyloxy-5β-androst-6-en-17-one;

11. hydrolysing the 3-acyloxy group to form 3β,5-dihydroxy-15β,16β-methylene-5β-androst-6-en-17-one;

12. methylenating the $\Delta^6$-double bond to form 3β,5-dihydroxy-6β,7β;15β,16β-dimethylene-5β-androstan-17-one;

13. reacting the latter with propargyl alcohol to form 17α-(3-hydroxy-1-propynyl)-6β,7β;15β,16β-dimethylene-5β-androstane-3β,5,17β-triol;

14. hydrogenating the latter to form 17α-(3-hydroxypropyl)-6β,7β;15,16β-dimethylene-5β-androstane-3β,5,17β-triol; and 15. oxidizing the latter with lactone formation resulting in 6β,7β;15β,16β-dimethylene-3-oxo-17α-pregn-4-ene-21,17-carbolactone;

In contrast, by using the 3β,7β,15α-trihydroxy-5-androsten-17-one of this invention as the intermediate, the desired 6β,7β;15β,16β-dimethylene-3-oxo-17α-pregn-4-ene-21,17-carbolactone can be obtained advantageously as follows by conducting the synthesis with the same starting material:

1. microbiologically hydroxylating 3β-hydroxy-5-androsten-17-one in the 7α- and 15α-positions;

2. epimerizing the 7α-hydroxy group in the resultant compound according to the process of this invention to obtain the 7β-hydroxy group;

3. partially esterifying the 3β- and 15α-hydroxy groups in the resultant compound with pivalic acid;

4. conventionally introducing the 15β,16β-methylene group in the resultant compound, according to Corey and Chaykovsky, J. Am. Soc. 84 (1962) 3782; and 5–12. these steps are identical to synthesis stages 8–15 described above and are listed as Examples A through H herein for the commercial exploitation of the compound of this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Preparation of the Starting Material

A 2-liter Erlenmeyer flask containing 500 ml of a nutrient solution sterilized in an autoclave for 30 minutes at 120° C. and made up of 3.0% dextrose monohydrate, 1.0% corn steep liquor, 0.2% sodium nitrate, 0.1% potassium dihydrogen phosphate, 0.2% dipotassium hydrogen phosphate, 0.05% magnesium sulfate heptahydrate, 0.002% iron sulfate heptahydrate, and 0.05% potassium chloride is inoculated with a slanted-tube culture of the strain Colletotrichum lini (CBS 11221) and shaken for 3 days at 30° C. on a rotary shaker at 165 rpm.

250 ml of this incubation culture is utilized to inoculate a 20-liter preliminary fermentor filled with 15 l of a medium having the same composition as the incubation culture and sterilized at 120° C. and 1.1 atm. gauge for 60 minutes. Adding a defrother on silicone basis, germination is conducted at 29° C. and under 0.7 atm. gauge pressure with aeration (15 l/min) and agitation (220 rpm) for 33 hours.

Thereafter 0.9 l of this culture is withdrawn under sterile conditions and used for inoculating a 20-liter main fermentor containing 14 l of a nutrient medium sterilized as above and made up of 1.0% dextrose monohydrate, 1.0% corn steep liquor, 1.0% soybean meal, 0.2% sodium nitrate, 0.1% potassium hydrogen phosphate, 0.2% dipotassium hydrogen phosphate, 0.05% magnesium sulfate heptahydrate, 0.002% iron sulfate heptahydrate, and 0.05% potassium chloride. After an incubating phase of 12 hours under preliminary fermentor conditions, a sterile-filtered solution of 15 g of 3β-hydroxy-5-androsten-17-one in 115 ml of dimethylformamide is added thereto; the mixture is further agitated and aerated. The progress of fermentation is controlled by sampling; these samples are extracted with methyl isobutyl ketone and analyzed by thin-layer chromatography. After a contact period of 24 hours, the reaction is completed. The culture broth is then extracted once with half the culture volume and then twice with respectively one-third the culture volume, with methyl isobutyl ketone; the extracts are combined and concentrated in a forced circulation evaporator to about 1 liter. The concentrate is thereafter concentrated on a rotary evaporator at a bath temperature of 50° C. to about 200 ml and stored overnight in a refrigerator. The thus-precipitated crystallized product is vacuum-filtered, washed with a small amount of cold methyl isobutyl ketone, and dried for 8 hours at 80° C. in a vacuum drying cabinet. Yield: 11.2 g of 3β,7α,15α-trihydroxy-5-androsten-17-one, mp 214°–215° C.

The mother liquor is concentrated to dryness under vacuum, the oily-crystalline residue is washed twice with respectively 100 ml of hexane to remove the defrother, then take up in methyl isobutyl ketone, and recrystallized therefrom, thus obtaining 1.8 g of a secondary crystallization product, mp 208°–210° C.

Preparation of the starting material can also be executed by using as the substrate for the microbiological dihydroxylation 3β-acetoxy-5-androsten-17-one instead of 3β-hydroxy-5-androsten-17-one. In this case, the microorganism saponifies additionally the acetate prior to the hydroxylation. The fermentation conditions remain unchanged.

EXAMPLES FOR COMMERCIAL USABILITY OF THE COMPOUNDS OF THIS INVENTION

EXAMPLE A

A suspension of 160 g of 7β-hydroxy-15β,16β-methylene-3β-pivaloyloxy-5-androsten-17-one in 1600 ml of toluene is combined at 80° C., after addition of 1.6 g of vanadium(IV) oxide acetylacetonate, within 2 hours with 160 ml of 80% tert-butyl hydroperoxide in 475 ml of toluene. After cooling, the solution is washed with water, dried over sodium sulfate, and evaporated under vacuum. Yield: 171 g of 5,6β-epoxy-7β-hydroxy-15β,16β-methylene-3β-pivaloyloxy-5β-androstan-17-one. A sample recrystallized from acetonehexane melts at 219°–220° C.

$[\alpha]_D = -12°$ (chloroform).

EXAMPLE B

A solution of 169 g of 5,6β-epoxy-7β-hydroxy-15β,16β-methylene-3β-pivaloyloxy-5β-androstan-17-one in a mixture of respectively 340 ml of dichloromethane, tetrachloromethane, and pyridine is combined with 200 g of triphenylphosphine and stirred for 2 hours at room temperature. The reaction solution is washed with water, dried over sodium sulfate, and evaporated to dryness under vacuum. The residue is agitated with 310 ml of ethanol and filtered. The filter cake is washed with 175 ml of ethanol and dried under vacuum. Yield: 139.2 g of 7α-chloro-5,6β-epoxy-15β,16β-methylene-3β-pivaloyloxy-5β-androstan-17-one. A sample recrystallized from acetone-hexane has a melting point of 227°–228° C.

$[\alpha]_D = -100°$ (chloroform).

EXAMPLE C

A solution of 196 g of 7α-chloro-5,6β-epoxy-15β,16β-methylene-3β-pivaloyloxy-5β-androstan-17-one in 500 ml of acetic acid and 800 ml of tetrahydrofuran is combined at 70° C. with 392 g of zinc dust in two portions at an interval of 30 minutes and stirred for one hour at this temperature. After cooling, the zinc is filtered off over "Celite" and washed with 5 l of methylene chloride. The combined filtrates are combined with 1.5 l of water and neutralized under agitation by adding solid sodium bicarbonate. The organic phase is then washed with water, dried over sodium sulfate, and concentrated under vacuum. By trituration of the resultant solid product with ethyl acetate, 134.7 g of 5-hydroxy-15β,16β-methylene-3β-pivaloyloxy-5β-androst-6-en-17-one is obtained, mp 242°≧243° C.

EXAMPLE D 134 g of 5-hydroxy-15β,16β-methylene-3β-pivaloyloxy-5β-androst-6-en-17-one is dissolved in 1340 ml of tetrahydrofuran and 670 ml of methanol and combined in succession with 40 g of pulverized potassium hydroxide and 13 g of sodium perchlorate. After 2.5 hours, the mixture is stirred into 8 l of water, neutralized with 20% sulfuric acid, and the precipitated solid product is removed by filtration. After dissolving in methylene chloride and drying with sodium sulfate, the product is concentrated under vacuum. By trituration of the resultant solid compound with ethyl acetate, 99.8 g of 3β,5-dihydroxy-15β,16β-methylene-5β-androst-6-en-17-one is obtained, mp 196.5°–198° C.

EXAMPLE E

A solution of 26 g of 3β,5-dihydroxy-15β,16β-methylene-5β-androst-6-en-17-one in 520 ml of ethylene glycol dimethyl ether is stirred for 4 hours at 80° C. with 78 g of zinc-copper and 69 ml of methylene iodide. The mixture is then diluted with methylene chloride, washed with saturated ammonium chloride solution and water, dried, and evaporated. The residue is chromatographed on silica gel, thus obtaining 16.3 g of 3β,5-dihydroxy-6β,7β;15β,16β-dimethylene-5β-androstan-17-one, mp 205.5°–207° C.

EXAMPLE F 25.1 g of 3β,5-dihydroxy-6β,7β;15β,16β-dimethylene-5β-androstan-17-one is dissolved in 500 ml of tetrahydrofuran. Under cooling to 0° C. and under an argon atmosphere, 75.5 g of potassium methylate is added to this solution and then, under agitation, 50.4 ml of propargyl alcohol in 104 ml of tetrahydrofuran is added dropwise thereto in the form of a solution. The reaction mixture is stirred for 20 hours at 0° C. and poured into ice water. After neutralization with dilute sulfuric acid, the resultant precipitate is filtered off and dried. The crude product is chromatographed on silica gel, yielding 25 g of 17α-(3-hydroxy-1-propynyl)-6β,7β;15β,16β-dimethylene-5β-androstane-3β,5,17β-triol; mp 202°–203° C. (acetone).

EXAMPLE G 24.5 g of 17α-(3-hydroxy-1-propynyl)-6β,7β;15β,16β-dimethylene-5β-androstane-3β,5,17β-triol is hydrogenated in 250 ml of tetrahydrofuran and 125 ml of methanol in the presence of 3.75 g of palladium on carbon (10% strength) and 0.5 ml of pyridine until 2 equivalents of hydrogen have been absorbed. The product is filtered off from the catalyst and evaporated, thus obtaining 24.7 g of 17α-(3-hydroxypropyl)-6β,7β;15β,16β-dimethylene-5β-androstane-3β,5,17β-triol which is used in the subsequent stage without further purification.

EXAMPLE H

A solution of 24.7 g of 17α-hydroxypropyl)-6β,7β;15β,16β-dimethylene-5β-androstane-3β,5,17β-triol in 247 ml of pyridine is combined with a solution of 74.1 g of chromium(VI) oxide in 247 ml of water and 494 ml of pyridine and stirred for 16 hours at 50° C. Then the mixture is diluted with methylene chloride, washed with water, dried, and evaporated. The residue is chromatographed on silica gel. Recrystallization from diisopropyl ether-acetone yields 14.5 g of 6β,7β;15β,16β-dimethylene-3-oxo-17α-pregn-4-ene-21,17-carbolactone, mp 196.5°–197.5° C.

The following examples relate to the process of this invention per se.

EXAMPLE 1

1.5 g of 3β,7α,15α-trihydroxy-5-androsten-17-one is suspended in a mixture of 40 ml of dichloromethane and 20 ml of acetone and heated under reflux to boiling on a steam bath until complete dissolution occurs. Then a weak nitrogen stream is passed over the solution and the latter is allowed to cool to about 5° C. under agitation by external ice cooling. As soon as the dissolved androstenetriol begins to reappear in flakes, 10 ml of a freshly prepared mixture of 9 ml of acetone and 1 ml of 35% perchloric acid (70% perchloric acid 1:1 diluted with water) is added thereto in a single portion, thus redissolving the intermediately precipitated flakes. After 10-20 minutes of agitation at room temperature under nitrogen, the solution begins to become turbid due to precipitation of a portion of the epimerized product.

After a total of 20 hours of reaction time, the reaction mixture is combined with 5 ml of pyridine, stirred for 5 minutes, and the mixture is then evaporated on a rotary evaporator at a bath temperature of 60° C. under vacuum. A pyridine-containing crystalline slurry remains which is combined with 200 ml of ice water and stirred for 2 hours at room temperature. The thus-precipitated crystalline product is vacuum-filtered, washed thoroughly with water, and dried at 50° C. in a vacuum drying cabinet until constant weight is obtained. Yield: 1.3 g of 3β,7β,15α-trihydroxy-5-androsten-17-one, mp 166°-169° C.

A sample recrystallized twice from acetoneisopropyl ether melts at 180°-182° C.

EXAMPLE 2

One gram of 3β,7β,15α-trihydroxy-5-androsten-17-one is dissolved at room temperature in 20 ml of pyridine; 2 ml of pivalic acid chloride as well as 100 mg of 4-dimethylaminopyridine are added to the reaction mixture, and the latter is agitated at room temperature for 48 hours. The reaction mixture is then poured into 250 ml of ice water, stirred for 2 hours at room temperature, the resultant precipitate is vacuum-filtered, washed with water, and dried for 8 hours in a vacuum drying cabinet at 50° C., yielding 1.38 g of 7β-hydroxy-3β,15α-dipivaloyloxy-5-androsten-17-one, mp 195°-197° C.

EXAMPLE 3

10 g of 3β,7α,15α-trihydroxy-5-androsten-17-one is suspended in 200 ml of methyl isobutyl ketone and combined under vigorous agitation at 20° C. within 5 minutes dropwise with 3.5 ml of 35% perchloric acid (1.75 ml of HClO$_4$ conc.+1.75 ml of H$_2$O). After 4 hours of agitation at 20° C., the reaction mixture is cooled to −10° C. and stirred for another 2 hours at this temperature. The mixture is then vacuum-filtered, washed twice with 30 ml of cooled methyl isobutyl ketone, and the filter residue is dissolved in 200 ml of pyridine. The pyridine solution is then combined with 2 g of 4-dimethylaminopyridine as well as 20 ml of pivalic acid chloride; the mixture is placed in a heating bath of 50° C. and agitated for 4 hours. The reaction mixture is thereafter poured into 1 liter of ice water, stirred for another hour, finally vacuum-filtered, thoroughly washed with water, and dried overnight in a vacuum drying chamber at 60° C. Yield: 13.7 g of 7β-hydroxy-3β,15α-dipivaloyloxy-5-androsten-17-one, mp 197°-199° C.

EXAMPLE 4

Under heating, 1.5 g of 3β,7α,15α-trihydroxy-5-androsten-17-one is dissolved in a mixture of 30 ml of 2-butanone and 30 ml of dichloromethane. After cooling to room temperature, 10 ml of a freshly prepared mixture of 9 ml of 2-butanone and 1 ml of 35% sulfuric acid is added thereto and the mixture stirred for 30 minutes at room temperature. Subsequently the reaction mixture is combined with 5 ml of pyridine and the mixture evaporated at 60° C. under vacuum. The residue is mixed with 200 ml of ice water and agitated for 2 hours. The thus-precipitated crystallized product is vacuum-filtered, washed with water, and dried. Yield: 1.4 g of 3β,7β,15α-trihydroxy-androsten-17-one, mp 162°-164° C.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing 3β,7β,15α-trihydroxy-5-androsten-17-one, comprising acidifying 3β,7β,15α-trihydroxy-5-androsten-17-one with a dilute mineral acid or dilute strong organic acid in the presence of a ketone, and, then, reacting the resultant product with and organic base.

2. A process of claim 1 wherein the acidification is conducted in the presence of a solvent.

3. A process of claim 1 wherein the acid is sulfuric acid, perchloric acid, hydrochloric acid, p-toluenesulfonic acid or trifluoroacetic acetic acid of 10-50 vol. % strength.

4. A process of claim 1 or 3 wherein the ketone is aliphatic and contains up to 6 carbon atoms and is contained in the reaction medium in an amount of 10-100 molar equivalents based on the amount of starting material employed.

5. A process of claim 1 or 3 wherein the base is pyridine.

6. A process of claim 4 wherein the base is pyridine.

7. A process of claim 1 for preparing the 3,15-dipivalate of the resultant 3β,7β,15α-triol, comprising esterifying the resultant 3β,7β, 15α-triol in the 3β- and 15α-positions with pivalic acid or a reactive derivative thereof.

8. A process of claim 3 wherein the acidification is conducted at 0°-50° C. for 1-24 hours and the subsequent treatment with base is conducted at 5°-50° C. for 2-48 hours.

9. A process of claim 4 wherein the acidification is conducted at 0°-50° C. for 1-24 hours and the subsequent treatment with base is conducted at 5°-50° C. for 2-48 hours.

10. A process for epimerizing an allyl-positioned 7α-hydroxy or 7α-o-acetoxy group in a Δ$^5$-steroid to the corresponding 7β-group, comprising treating the 7α-steroid with a dilute mineral acid or dilute strong organic acid in the presence of a ketone.

11. A process of claim 10 further comprising adding a base to the product of said treatment step.

12. 3β,7β,15α-Trihydroxy-5-androsten-17-one.

13. 3β,15α-Dipivaloyoxy-7β-hydroxy-5-androsten-17-one.

14. In a process for preparing 6β,7β;15β,16β-dimethylene-3-oxo-17α-pregn-4-ene-21,17-carbolactone from 7β-hydroxy-15β,16β-methylene-3β-pivaloyloxy-5-androsten-17-one, the improvement wherein the latter compound is prepared by,
carrying out the process of claim 7 in order to prepare the 3,15-dipivalate of 3β,7β,15α-trihydroxy-5-androsten-17-one, and
methylenating the 15β,16β-position in the resultant compound to form 7β-hydroxy-15β,16β-methylene-3β-pivaloyloxy-5-androsten-17-one.

* * * * *